US009465019B2

(12) United States Patent
Lockhart et al.

(10) Patent No.: US 9,465,019 B2
(45) Date of Patent: Oct. 11, 2016

(54) MOUNTABLE SENSOR FOR AN AIRCRAFT

(71) Applicant: Blue Storm Associates, Inc., Fairfax Station, VA (US)

(72) Inventors: Mary Lockhart, Fairfax Station, VA (US); Thomas Wallace, Arlington, VA (US); Randal Brumbaugh, Altadena, CA (US); Malcolm Robbie, Stow, OH (US); Brian Patterson, Centennial, CO (US); Donna Blake, Oakton, VA (US); Andreas Goroch, Salinas, CA (US)

(73) Assignee: Blue Storm Associates, Inc., Fairfax Station, VA (US)

( * ) Notice: Subject to any disclaimer, the term of this patent is extended or adjusted under 35 U.S.C. 154(b) by 200 days.

(21) Appl. No.: 14/011,454

(22) Filed: Aug. 27, 2013

(65) Prior Publication Data
US 2014/0053628 A1     Feb. 27, 2014

Related U.S. Application Data

(60) Provisional application No. 61/693,410, filed on Aug. 27, 2012.

(51) Int. Cl.
| | |
|---|---|
| *G01N 33/00* | (2006.01) |
| *G01N 25/58* | (2006.01) |
| *G01W 1/00* | (2006.01) |
| *G08B 1/08* | (2006.01) |
| *G06F 7/60* | (2006.01) |
| *G01S 13/00* | (2006.01) |

(52) U.S. Cl.
CPC .......... *G01N 33/0016* (2013.01); *G01N 25/58* (2013.01); *G01N 33/0009* (2013.01); *G01N 33/0011* (2013.01); *G01S 13/00* (2013.01); *G01W 1/00* (2013.01); *G06F 7/60* (2013.01); *G08B 1/08* (2013.01)

(58) Field of Classification Search
None
See application file for complete search history.

(56) References Cited

U.S. PATENT DOCUMENTS

| | | | | |
|---|---|---|---|---|
| 6,412,731 | B1 * | 7/2002 | Gabriel | 244/12.1 |
| 6,941,806 | B2 * | 9/2005 | Burns et al. | 73/170.02 |
| 7,177,785 | B2 * | 2/2007 | Hartmann et al. | 703/2 |
| 7,760,084 | B2 * | 7/2010 | Jensen et al. | 340/539.26 |
| 2010/0253567 | A1 * | 10/2010 | Factor et al. | 342/52 |

* cited by examiner

*Primary Examiner* — Paul West
(74) *Attorney, Agent, or Firm* — Davidson Berquist Jackson & Gowdey, LLP

(57) ABSTRACT

A sensor system runs real-time software on the processor to receive and log temperature and humidity data from the sensors. A processor processes the data, reformats the data packaged with GPS information provided by the centralized sensor control system for transmission to the platform receiver (including error checking), and provides a diagnostic interface for displaying logged data and status information. This data is time stamped and transmitted to the centralized sensor control system across the external control/data interface.

19 Claims, 5 Drawing Sheets

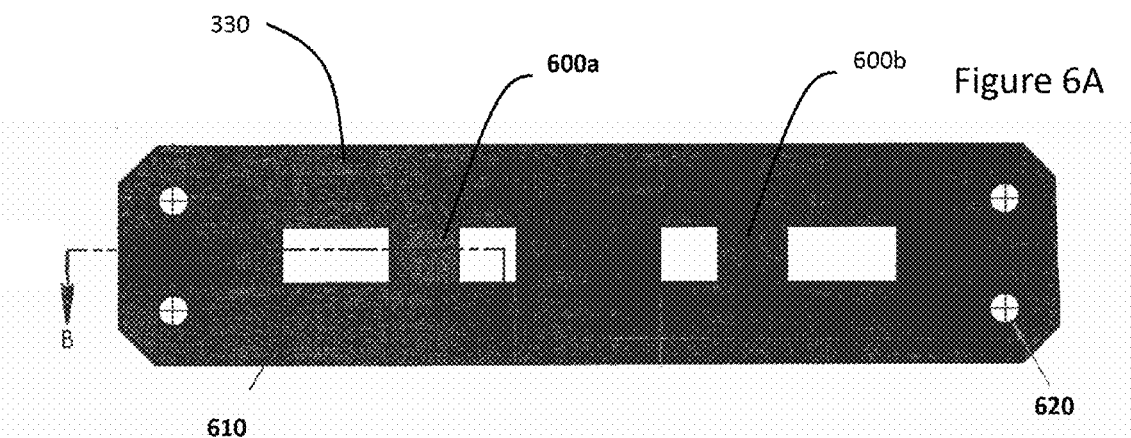
Figure 6A
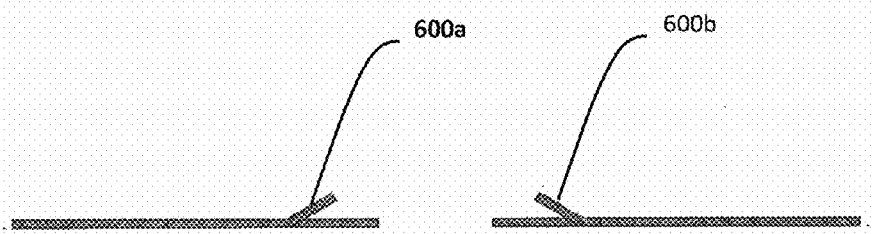
Figure 6B
Figure 6C

MOUNTABLE SENSOR FOR AN AIRCRAFT

CROSS REFERENCE TO CO-PENDING APPLICATION

This application is a non-provisional application claiming the benefit of U.S. Provisional Patent Application No. 61/693,410, filed Aug. 27, 2012, the contents of which are incorporated herein by reference.

GOVERNMENT LICENSE RIGHTS

This invention was made with government support under contract FA8750-09-D-0022-0014 awarded by the Department of the Air Force. The government has certain rights in the invention.

FIELD OF INVENTION

The present invention is directed to mountable sensors in aircraft, and, in one embodiment, to a mountable temperature and relative humidity sensor for use with remotely piloted aircraft (RPA).

DISCUSSION OF THE BACKGROUND

Known remotely piloted aircraft currently have limited resource protection in that their environmental/atmospheric sensors are inadequate to detect certain conditions that put the asset (i.e., the RPA) in danger from environmental/atmospheric conditions.

BRIEF DESCRIPTION OF THE DRAWINGS

The following description, given with respect to the attached drawings, may be better understood with reference to the non-limiting examples of the drawings, wherein:

FIGS. 6A-6C and are a top view and two side views of the flow diverter of FIG. 2.

DISCUSSION OF THE PREFERRED EMBODIMENTS

Figure 1:
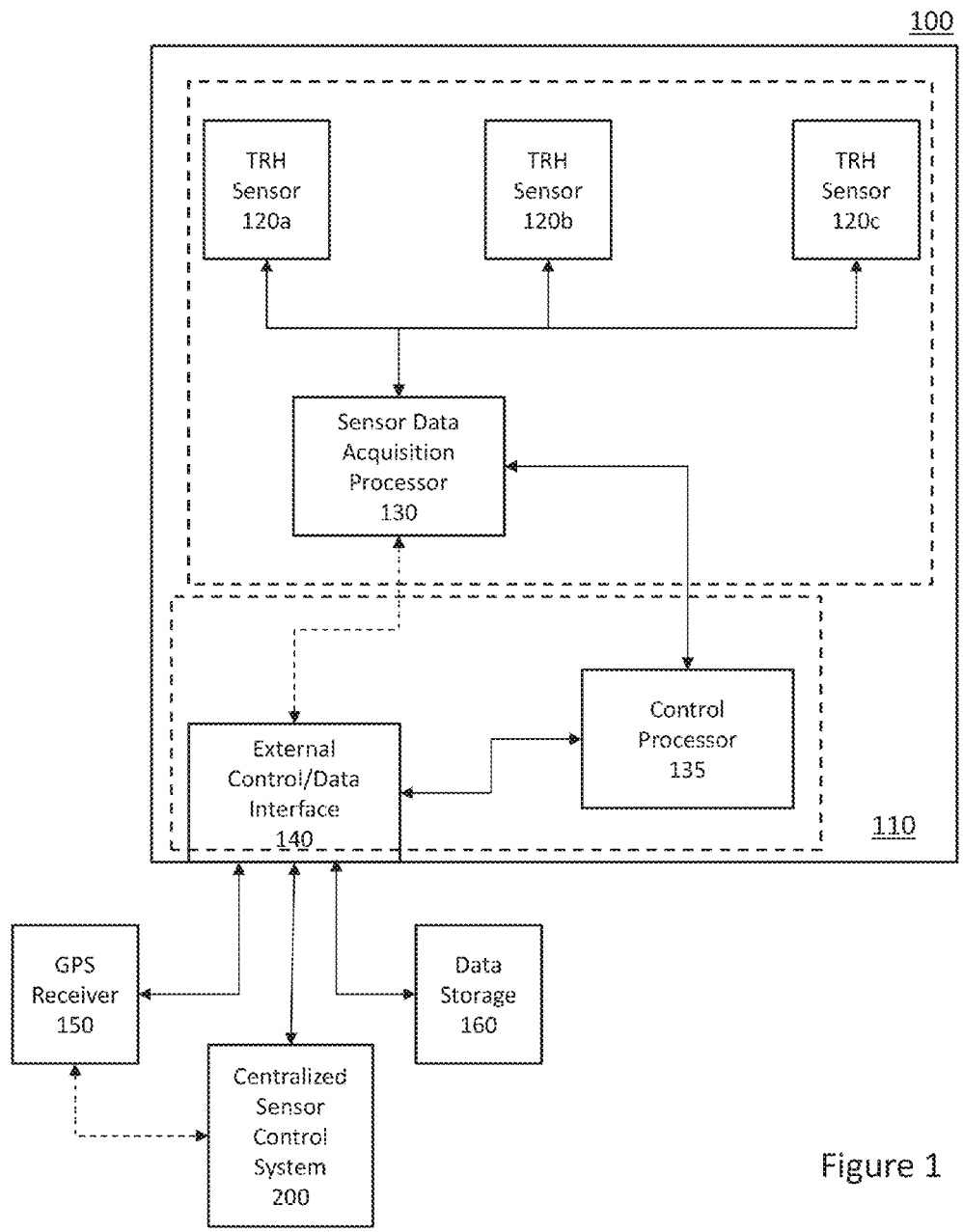
FIG. 1 is a simplified block diagram of an exemplary environment for performing environmental/atmospheric sensing to aid in the protection of aircraft (including remotely piloted aircraft (RPA))

Turning to FIG. 1, an exemplary system 100 is illustrated in which a sensor system 110 interacts through an external control/data interface 140 (having one or more ports) while performing environmental/atmospheric sensing to aid in the protection of aircraft (including remotely piloted aircraft (RPA)), such as airplanes and helicopters. In the illustrated embodiment, at least a first port of the external control/data interface 140 is connected to a GPS receiver 150 to provide GPS data to the sensor system 110. However, in an alternate embodiment, the sensor system 110 may instead include an integrated GPS receiver to enable the sensor system 110 to be more self-contained. As also shown in FIG. 1, the external control/data interface 140 may include a second port, which may be the same or different than the first port, for storing data from the sensor system 110 to a data storage system 160. As also shown in FIG. 1, the external control/data interface 140 may include a third port, which may be the same or different than the first and second ports, for connecting the sensor system 110 to an externally connected computer (e.g., a centralized sensor control system 200 for data retrieval, programming and/or debugging). The first and third ports for connecting to the data storage system 160 and the externally connected computer may be custom interfaces or any one or more of various standard data transfer interfaces (e.g., serial interfaces (such as USB, USB 2.0, USB 3.0, I2C, or Thunderbolt), parallel interfaces, wired-network interfaces (e.g., Ethernet) or wireless network interfaces (e.g., any of the 802.11 family of protocols)). The second port for connecting to the data storage system 160 may be a custom interface or any one or more of various standard data transfer interfaces (e.g., interfaces for removable flash memory cards (such as SD, SDHC, MemoryStick, or CompactFlash), serial interfaces (such as USB, USB 2.0, USB 3.0, I2C, or Thunderbolt), parallel interfaces, wired-network interfaces (e.g., Ethernet) or wireless network interfaces (e.g., any of the 802.11 family of protocols)). As shown in FIG. 1, the sensor system 110 may alternatively receive the GPS location information from the centralized sensor control system 200 instead of utilizing a separate connection to the system 110. Any of the first through third ports may supply power to the sensor system 110, or the sensor system may be connected to power via a power adapter, or the sensor system may be self-powered (e.g., battery powered). In an exemplary embodiment, power (e.g., 28V) is provided via the second port to ensure a controlled voltage source that is common to multiple instruments/sensors which are each connected to the centralized sensor control system 200.

As shown in FIG. 1, the sensor system 110 may be constructed from a number of interconnected sub-components; however, the sensor system 110 may alternatively have one or more of the sub-components integrated into fewer or more parts than shown. In the illustrated embodiment, the sensor system 110 includes a number of temperature and relative humidity sensors (TRH sensors) 120a-120c (collectively referred to as 120), although additional types of sensors could also be provided. The number of TRH sensors 120 may be chosen based on certain design criteria related to an actual environment of use of the sensor system 110, but three TRH sensors 120 will be described herein without a loss of generality.

As shown in FIG. 1, the TRH sensors 120 are configured such that their data (or a subset of their data) can be sent via the external control/data interface 140 for analysis and/or storage. The exemplary embodiment of FIG. 1 utilizes two processors and their corresponding memories (not shown) to handle the data acquisition and pre-processing before passing the subset of the data to the external control/data interface 140; however, a single processor or several processors also could be utilized instead. For example, processors 130 and 135 and interface 140 could be built together in a system-on-a-chip (SOC).

The external control/data interface 140 may be connected to a centralized sensor control system 200 that collects real-time data from a number of sensor systems. For example, the centralized sensor control system 200 may be a SmartNode Pod from Northrup Grumman, and the data sent from the sensor system 110 would then be configured to send a subset of the data using a protocol and format understood by the SmartNode Pod. Similarly, in such a configuration, the communications link (e.g., cable) between the external control/data interface 140 and the centralized sensor control system would be a link that is compatible with a connection to the SmartNode Pod. (As used herein, a "subset" of the sensor data may be a proper subset that includes all of the sensor data.)

As shown in the exemplary embodiment of FIG. 1, a number of TRH sensors 120a-c are connected to a data acquisition processor 130 which is used to perform voltage and protocol translation from the physical interface of the TRH sensors to the digital format utilized for subsequent processing internal to the sensor system 110. For example, the processor 130 may perform digital-to-analog conversion of TRH sensor outputs if their outputs are analog. The processor 130 may further perform buffering and control of the sensors 120 (and additional types of sensors, not shown). Such control of the sensors may include calibrations to control or adjust the readings of the sensors during bench testing, ground testing and/or in-flight testing/configuration.

Preferably, the TRH sensors 120 simultaneously measure humidity and temperature for calibration and consistency of data and are small enough to eliminate (or significantly reduce) the thermal inertia problem limiting response time of sensor. As described above, digital outputs are preferably used to minimize crosstalk and other signal quality issues, either by the TRH sensor outputting a digital value directly or by the processor 130 performing analog-to-digital conversion. Further, the use of multiple sensors provides redundancy and aids in calibration of individual sensors.

The converted data from the processor 130 is then transmitted to the control processor 135 across either an internal bus or an external data transfer interface. By utilizing an external data transfer interface, the TRH sensors 120 and the processor 130 may be separated from the control processor 135 by a larger physical distance (e.g., 10', 20', or more) than available for an internal bus. This may enable a wider range of placements of the various portions of the sensor system 110 in order to meet design parameters. For example, the TRH sensors 120 and processor 130 may be placed in a first housing that is separate from a second housing of the control processor such that only the first housing is partially exposed to atmospheric/environmental conditions (e.g., by being partially mounted through the exterior of the SmartNode Pod) while the second housing remains mounted inside the SmartNode Pod. This reduces a cross section of the portion of the sensor system that is exposed to the airflow of the aircraft and reduces drag. When utilizing an external data transfer interface, the external data transfer interface can be a custom interface or any one or more of various standard data transfer interfaces (e.g., serial interfaces (such as USB, USB 2.0, USB 3.0, I2C, or Thunderbolt), parallel interfaces, wired-network interfaces (e.g., Ethernet) or wireless network interfaces (e.g., any of the 802.11 family of protocols)).

The use of an external data transfer interface between the processors 130 and 135 may further allow quick access to either of the processors 130 and 135 for field testing, diagnostics and data download. For example, the external data transfer interface can be used by a diagnostic laptop to access the control processor 135 and request that previously stored data or logs be transferred, that diagnostics be run in-field or that software be updated. Similarly, the external data transfer interface may be connected to the processor 130 to allow testing of the sensors or reloading of software on the processor 130. Alternatively, the external data transfer interface may include a splitter which enables either the processor 130 or another processor to communicate with the processor 135 over the same interface.

Figure 2:
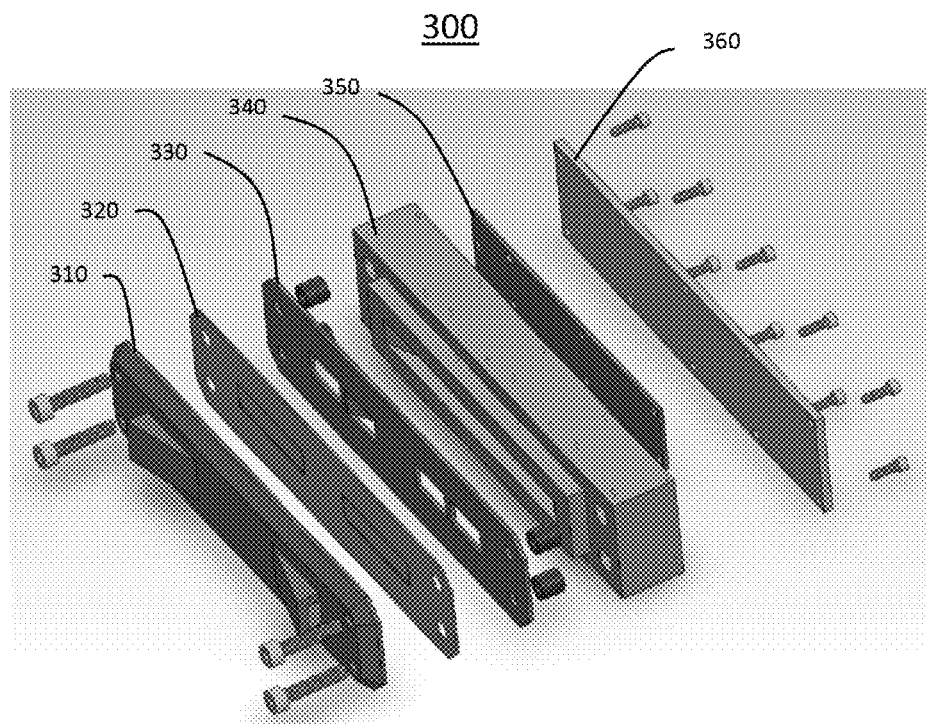
FIG. 2 is an expanded view of a first exemplary housing for the redundant sensors and sensor data acquisition processor of the sensor system of FIG. 1.
Figure 3:
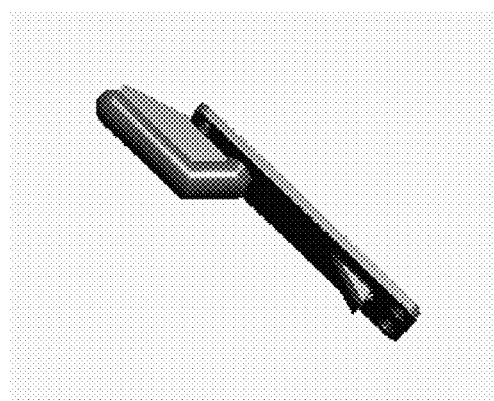
FIG. 3 is partial front view of an alternative front exterior cover for the housing of FIG. 2.
Figure 4:
FIG. 4 is a partial side view of a second exemplary housing for the redundant sensors and sensor data acquisition processor of the sensor system of FIG. 1 utilizing a different alternative front exterior cover than FIG. 2.

As shown in FIG. 2, a housing composed of a number of portions surrounds the TRH sensors 120 and the processor 130. The housing is designed to be mounted on an exterior of the aircraft, such as on the SmartNode Pod of an RPA. From left-to-right, the housing includes a front exterior cover 310 (with air ducts acting as an intake and an outlet for airflow), a screen 320, a flow diverter 330 (with angled openings), a sensor plate 340, the circuit board 350 for mounting the sensors 120 and the processor 130, and a back cover plate 360. The back cover plate 360 receives a set of screws for holding various portions together, and the front exterior cover 310 is also held on with screws to allow access to the screen (to remove trapped foreign objects) while the housing is in the mounted position and/or to change the air ducts for use in different environments. FIG. 3 illustrates an alternative front exterior cover that can be used to replace the front exterior cover 310 of FIG. 2. Likewise, FIG. 4 illustrates an alternative front exterior cover that can be used to replace the front exterior cover 310 of FIG. 2. The air ducts can be replaced by removal of the exterior screws that mount the sensor box. Further, the screen is mounted behind the air duct to help eliminate foreign objects from entering the sensor.

Figure 5:
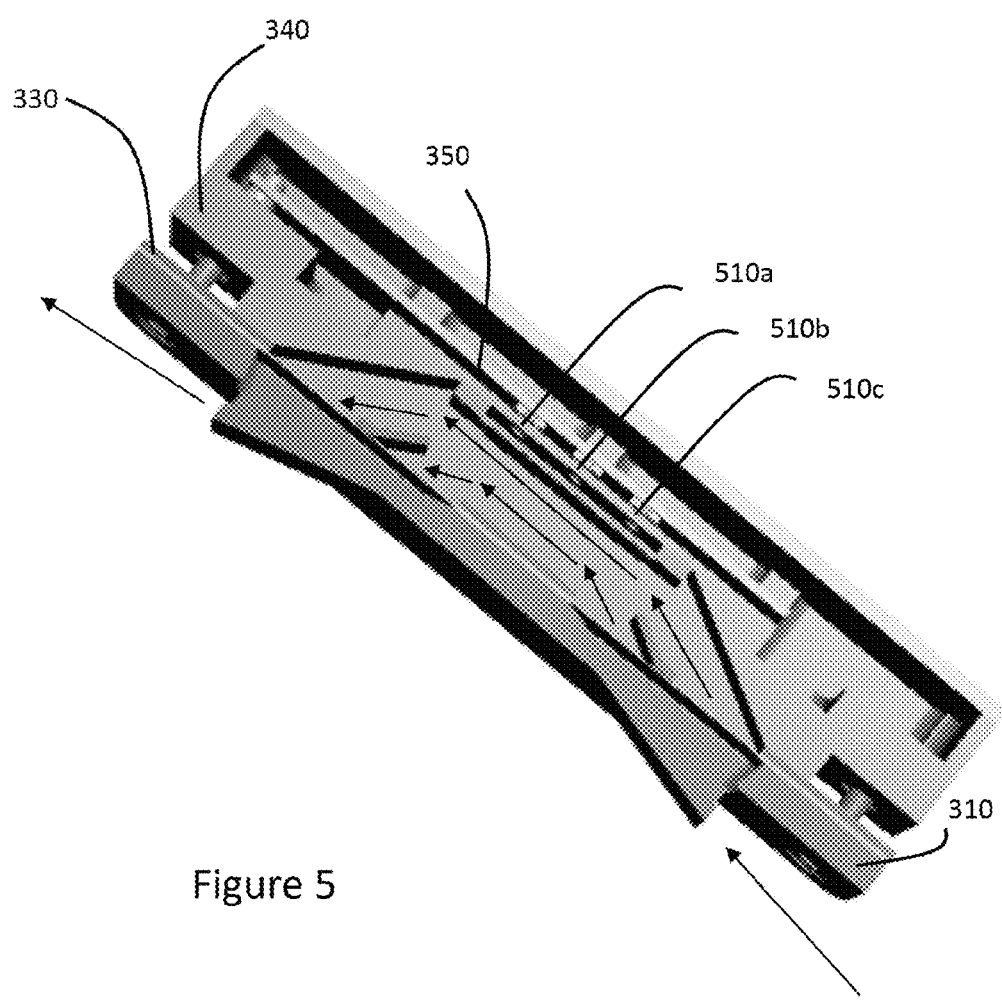
FIG. 5 is a cross sectional view of a portion of the first exemplary housing of FIG. 1.
Figure 7:
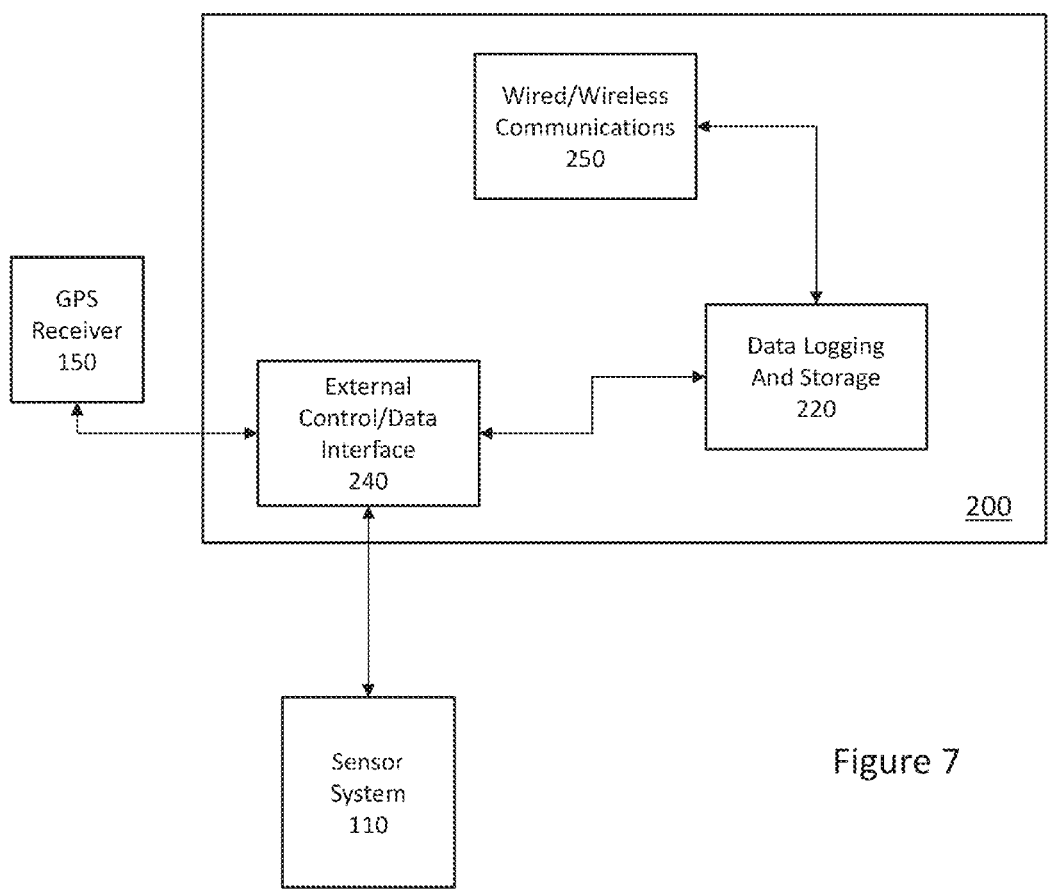
FIG. 7 is a simplified block diagram of a centralized sensor control system as shown in FIG. 1.

Using the configurations of FIGS. 2-4, the sensors 120 bleed representative air samples to provide a reasonable temperature and humidity, while not interfering with the pod aerodynamics. The use of redundant sensors on the internally mounted circuit board provides redundancy for sensor information as well as providing the capability to sample data at a fast enough rate to provide data for both asset protection and record weather data throughout an area for improved situational awareness and weather modeling. As seen in FIG. 5, an airflow diverter guides the air perpendicular to the sensors within the interior chamber of the sensor plate by passing the air above a set of holes 510a-c that communicate a small amount of air from the sensor plate 340 to the sensors without directly exposing the sensors to the airflow. Direct airflow may disrupt the sensing of changes for both temperature and relative humidity (and thus dew point derived from this data) and cause erroneous output from the sensor placing the aircraft in an increased area of risk to loss of mission or the aircraft itself. Although not shown, the back cover preferably includes a connector for receiving a cable that provides the data and power to the circuit board housing the TRH sensors 120 and the processor 130.

FIG. 6A shows a top view of the flow diverter 330. FIGS. 6B and 6C show partial side views of the flow diverter of FIG. 6A. The diverter arms 600a and 600b help to direct the air flow in the sensor plate 340, as shown in FIG. 5. As illustrated, the flow diverter also includes through holes (e.g., 620) for mounting the flow diverter 330 to the other components of FIGS. 2 and 5.

A second housing may be utilized to protect the circuit board mounting the control data processor 135 (and its memory) and the external control/data interface 140. The circuit board in the housing may further include additional circuitry such as a real-time clock for performing synchronization with the GPS information, a redundant temperature sensor, non-volatile memory for storage of TRH data and GPS coordinate information, and a non-real-time data transfer connection for post-flight data access. Such a housing may be mounted inside a SmartNode Pod (or inside a different portion of an aircraft) to receive data from and send control signals to the control data processor 135 and the external control/data interface 140 of the sensor system.

In general, the sensor system 110 runs real-time software on the processor 135 to receive and log temperature and humidity data from the sensors 120. The processor 135 processes the data, reformats the data packaged with GPS information provided by the centralized sensor control system 200 for transmission to the platform receiver (including error checking), and provides a diagnostic interface for displaying logged data and status information. This data is time stamped and transmitted to the centralized sensor control system 200 across the external control/data interface 140 (e.g., a USB or network connection). The sensor system 110 further is able to perform sensor health monitoring. In order to provide location context for the temperature and humidity data calculated from the sensor data, the processor 135 receives GPS time and location data from the GPS receiver 150. In the event that the GPS time and location data is formatted with additional data (e.g., UDP headers), the processor 135 removes or reformats that data as needed to perform the correlation between temperature and humidity data and the GPS location information. Also, to the extent that the centralized sensor control system 200 is expecting data be sent back to it in a particular format (e.g., combined TRH data, latitude, longitude, elevation, time, and sensor (GPS and/or TRH) status information) for storage/analysis, the processor 135 performs any data reformatting or packaging (e.g., by adding UDP header information to the TRH and GPS information) necessary prior to transmission to the centralized sensor control system 200. The processor 135 may further store temperature and humidity data to an on-board non-volatile memory interface (e.g., Flash memory or USB-based) for post-flight retrieval.

As discussed above, the sensor system 110 performs health/integrity testing on the sensors 120 and the processors 130/135 to verify proper operation of the system 110. In a first embodiment, the processor 135 polls (via the processor 130) the sensors 120a-c individually and then compares values between sensors and with previously collected data in order to determine a "valid" sensor response. All sensor data is averaged and a single value of temperature and relative humidity are stored for each latitude, longitude, elevation and time step. As shown in FIG. 6, this data is transmitted to the centralized sensor control system 200, received by a corresponding external control/data interface 240, stored in volatile and/or non-volatile memory of a data logging and storage system 220 and sent via a wireless communications device 250 (e.g., a satellite- or earth station-based communication adapter) to ground stations when data links are available. During climb-out on initial ascent and during final recovery descent, data will be stored internally to the sensor system 110 and can be recovered once data link capability becomes available. This same data transfer scheme is used during data link interruptions in-flight. Alternatively or additionally, the communications device 250 may also include a wired connection for post-flight data downloads. Though the system will report one temperature and relative humidity per location based on this averaging scheme, each of the three individual sensor's information is stored to allow error reporting and to be able to develop an RH gradient useful for asset protection.

A sensor that fails to respond to a measurement request, or that provides a response with an incorrect checksum, is marked as being in an error state. The states of all three sensors, as well as the number of total errors observed for each sensor since power up, are provided to the controller when requested. A sensor in an error state is commanded to soft reset each cycle of the event loop, and polling of that sensor continues as with a healthy sensor. If a sensor returns to providing data correctly, its status is updated to show that it is healthy again, but the total number of errors observed since power up is maintained for diagnostic purposes.

All raw sensor data and all other data sent via the external control/data interface 140 also are archived in the onboard non-volatile memory. Preferably, the data is stored in a FIFO manner such that when the memory is filled, archiving will continue by overwriting the oldest data in the memory. Environmental data stored in the onboard memory can be delivered via the external control/data interface 140 to the centralized sensor control system 200 upon request.

In an alternate embodiment, the processor 135 requests that the processor 130 poll each of the sensors 120a-c and provide to the processor 135 the average sensor data (along with any sensor status information). In such an embodiment, there is reduced communication between the processors 130 and 135, thereby enabling processor 135 to perform other functions.

The software running on the control processor 135 should also detect and report error conditions such as: no sensor present, one sensor failed, one sensor at lower limit of measurement bound, measurements occurred without GPS data, and transient communications failures on any of the communications interfaces.

While certain configurations of structures have been illustrated for the purposes of presenting the basic structures of the present invention, one of ordinary skill in the art will appreciate that other variations are possible which would still fall within the scope of the appended claims.

The invention claimed is:

1. A sensor system for performing measurement of environmental conditions affecting an aircraft, the sensor system comprising:
   an air intake duct for receiving air;
   a screen mounted behind the air intake duct for screening the received air;
   an air flow diverter, having first and second inlet holes, first and second outlet holes, and first and second diverter arms, for receiving the screened air having passed through the screen, for separating, using the first and second inlet holes, the screened air into first and second portions of the screened air, respectively, and for diverting, using the first diverter arm, paths of the first and second portions of the screened air;
   at least one environmental condition sensor for sensing an environmental condition in the second portion of the screened air; and
   an air outlet duct for outputting the first and second portions of the screened air after the at least one environmental condition sensor has sensed the environmental condition in the second portion of the screened air,
   wherein the air flow diverter diverts the second portion of the screened air perpendicular to the at least one environmental condition sensor, and
   wherein the second diverter arm directs the screened air through the first and second outlet holes to the air outlet duct.

2. The sensor system as claimed in claim 1, wherein the at least one environmental condition sensor comprises at least one temperature and relative humidity sensor.

3. The sensor system as claimed in claim 2, wherein the at least one temperature and relative humidity sensor comprises three temperature and relative humidity sensors.

4. The sensor system as claimed in claim 1, further comprising:
a processor for reading the environmental condition; and
a memory for storing the environmental condition read by the processor.

5. The sensor system as claimed in claim 4, further comprising a GPS receiver interface for receiving GPS location information corresponding to a location of the sensor system when the environmental condition was read.

6. The sensor system as claimed in claim 4, further comprising an external control/data interface for transmitting the environmental condition read by the processor to a device externally connected to the sensor system.

7. The sensor system as claimed in claim 6, further comprising a GPS receiver interface for receiving GPS location information corresponding to a location of the sensor system when the environmental condition was read, wherein the environmental condition read by the processor is transmitted to the device externally connected to the sensor system along with the location of the sensor system when the environmental condition was read.

8. The sensor system as claimed in claim 1, wherein the first inlet hole is smaller than the second inlet hole.

9. In an aircraft, the improvement comprising:
a sensor system for performing measurement of environmental conditions including:
an air intake duct for receiving air;
a screen mounted behind the air intake duct for screening the received air;
an air flow diverter, having first and second inlet holes, first and second outlet holes, and first and second diverter arms, for receiving the screened air having passed through the screen, for separating, using the first and second inlet holes, the screened air into first and second portions of the screened air, respectively, and for diverting, using the first diverter arm, paths of the first and second portions of the screened air;
at least one environmental condition sensor for sensing an environmental condition in the second portion of the screened air; and
an air outlet duct for outputting the first and second portions of the screened air after the at least one environmental condition sensor has sensed the environmental condition in the second portion of the screened air,
wherein the air flow diverter diverts the second portion of the screened air perpendicular to the at least one environmental condition sensor, and
wherein the second diverter arm directs the screened air through the first and second outlet holes to the air outlet duct.

10. The improvement as claimed in claim 9, wherein the at least one environmental condition sensor comprises at least one temperature and relative humidity sensor.

11. The improvement as claimed in claim 10, wherein the at least one temperature and relative humidity sensor comprises three temperature and relative humidity sensors.

12. The improvement as claimed in claim 9, further comprising:
a processor for reading the environmental condition; and
a memory for storing the environmental condition read by the processor.

13. The improvement as claimed in claim 12, further comprising a GPS receiver interface for receiving GPS location information corresponding to a location of the sensor system when the environmental condition was read.

14. The improvement as claimed in claim 12, further comprising an external control/data interface for transmitting the environmental condition read by the processor to a device externally connected to the sensor system.

15. The improvement as claimed in claim 14, further comprising a GPS receiver interface for receiving GPS location information corresponding to a location of the sensor system when the environmental condition was read, wherein the environmental condition read by the processor is transmitted to the device externally connected to the sensor system along with the location of the sensor system when the environmental condition was read.

16. The improvement as claimed in claim 9, wherein the aircraft is an airplane.

17. The improvement as claimed in claim 9, wherein the aircraft is a helicopter.

18. The improvement as claimed in claim 9, wherein the aircraft is a remotely piloted aircraft.

19. The improvement as claimed in claim 9, wherein the first inlet hole is smaller than the second inlet hole.

* * * * *